United States Patent [19]
Geissler et al.

[11] B 4,001,111
[45] Jan. 4, 1977

[54] DUAL TEMPERATURE GRADIENT ELUTION LIQUID CHROMATOGRAPHY

[75] Inventors: Paul R. Geissler, Edison; Robert P. Cahn, Millburn, both of N.J.

[73] Assignee: Exxon Research & Engineering Co., Linden, N.J.

[22] Filed: Mar. 19, 1974

[21] Appl. No.: 452,501

[44] Published under the second Trial Voluntary Protest Program on March 16, 1976 as document No. B 452,501.

[52] U.S. Cl. .................................... 210/24; 55/67
[51] Int. Cl.² ........................................ B01D 15/08
[58] Field of Search .......... 210/31 C, 24 C, 100 W; 55/67, 197

[56] References Cited
UNITED STATES PATENTS

| | | | |
|---|---|---|---|
| 3,654,145 | 4/1972 | Baunnock et al. | 55/67 X |
| 3,719,084 | 3/1973 | Walker | 55/197 X |
| 3,835,043 | 9/1974 | Geissler et al. | 210/31 C |

OTHER PUBLICATIONS
Heftmann, E. *Chromatography*, Reinhold Pub. Co. N. Y., p. 186, 1961.

*Primary Examiner*—John Adee
*Attorney, Agent, or Firm*—F. A. Santoro

[57] ABSTRACT

In a liquid chromatography commercial process for the separation of two or more components contained in admixture in a feedstream including the steps of (a) contacting the feedstream mixture containing the components to be separated with a bed of crystalline aluminosilicate adsorbent at conditions to effect the selective retention of two or more of the components by said adsorbent, (b) passing through said bed an eluent selected from the group consisting of aromatics and substituted aromatics, (c) increasing the strength of the eluting agent in the liquid carrier during the operation of the steps (a) and (b) above, (d) recovering from said bed a stream or streams containing at least a portion of the less selectively adsorbed components, and (e) recovering a stream substantially enhanced in concentration of said selectively adsorbed components relative to other components of feedstream wherein the improvement comprises preheating the eluting agent of step (c) above prior to passing it through said bed at temperatures of at least 160° C., to thereby effect the desired separation under conditions that cause substantially lower elution volume to feed ratios. The improved liquid chromatography process is particularly applicable to the separation of paraxylene and ethylbenzene from a C8 aromatic isomer mixture containing ethylbenzene. The above process when operated with the eluting agent preheating step at temperatures of about 160° C or higher causes temperature waves to flow through the bed with the final peak of each feed slug being eluted with the hotter eluting agent-carrier mixture, thus providing lower elution volume to feed ratios and thereby producing paraxylene more economically.

10 Claims, 5 Drawing Figures

DUAL TEMPERATURE GRADIENT
ELUTION CHROMATOGRAPHY PROCESS
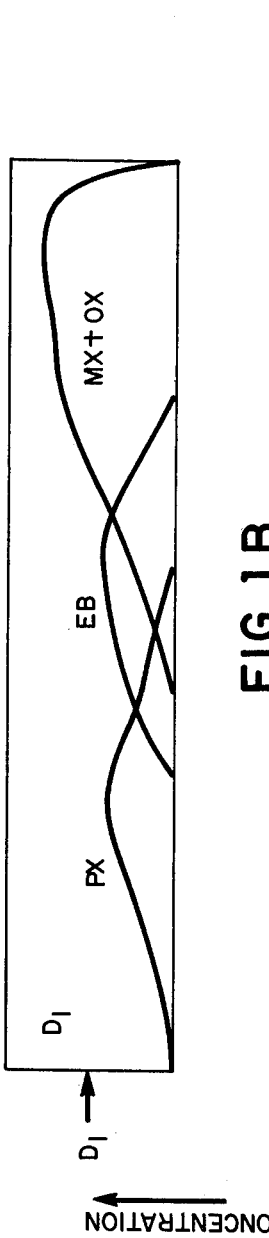
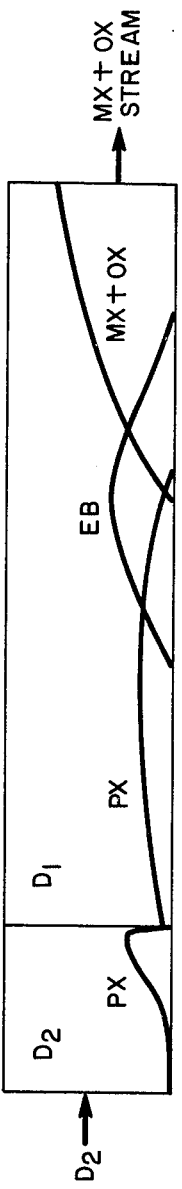
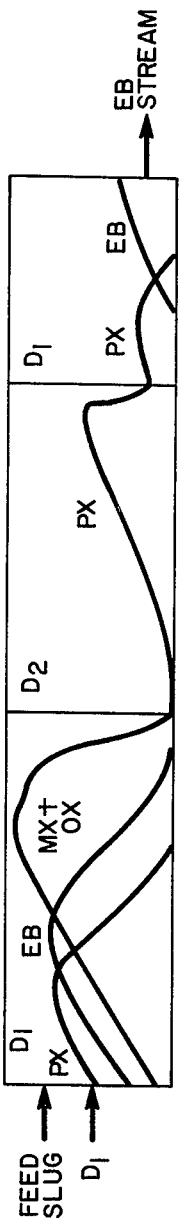
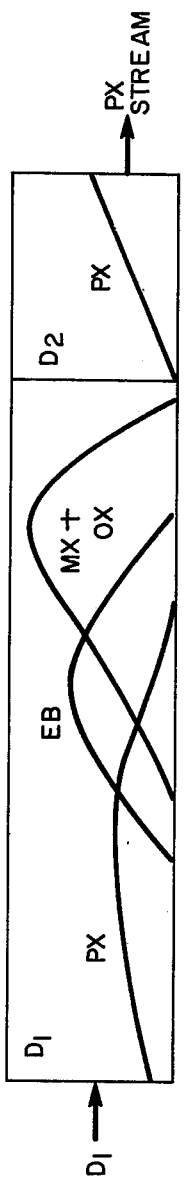

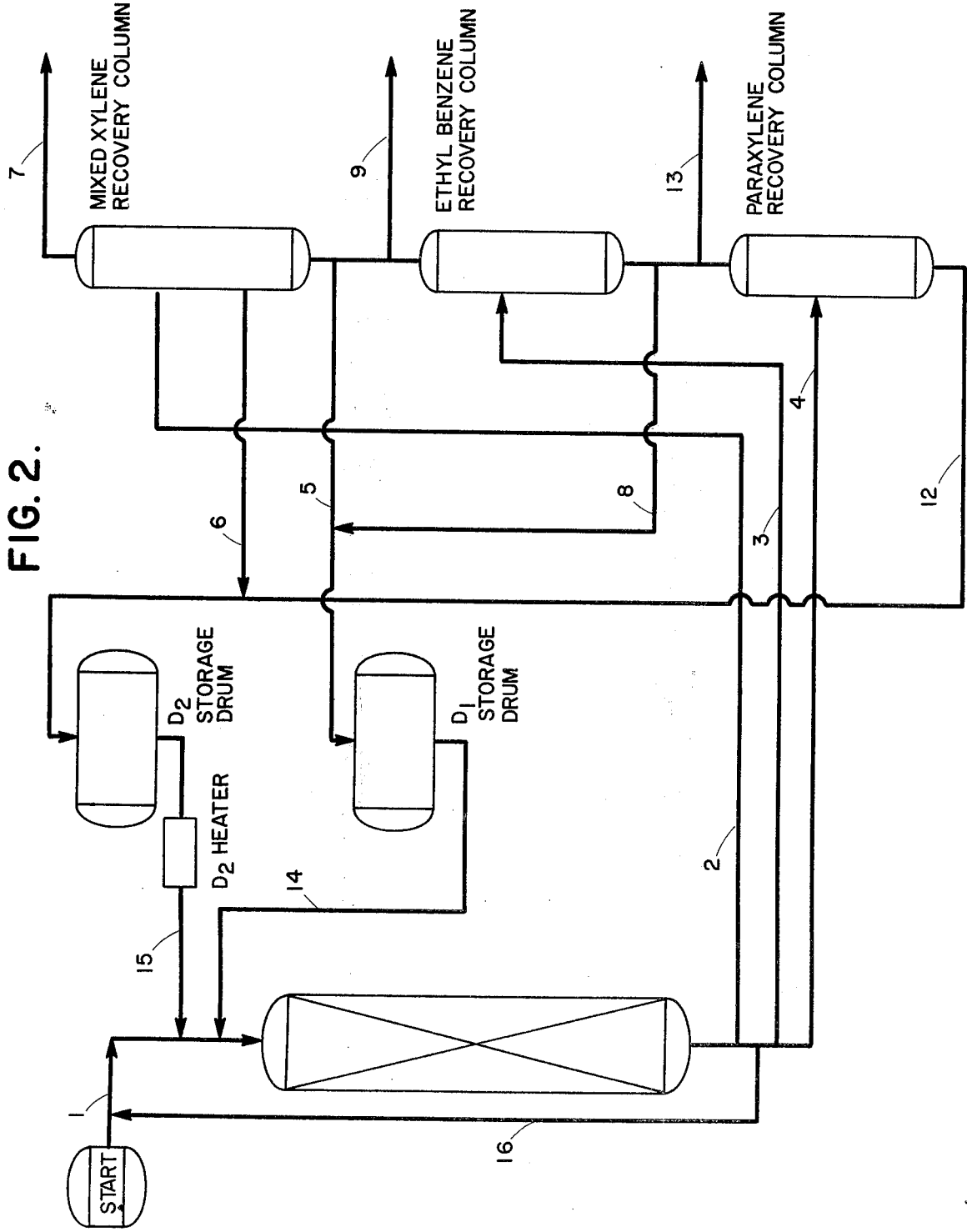

DUAL TEMPERATURE GRADIENT ELUTION LIQUID CHROMATOGRAPHY

FIELD OF THE INVENTION

This invention relates to an improvement in the operation of commercial liquid chromatographic separation processes of mixtures into two or more components. More particularly, the invention relates to an improved elution chromatographic separation process carried out in either two columns or in a single column. The separation of a $C_8$ aromatic isomer mixture is particularly adaptable to the operation of the present invention.

BACKGROUND OF THE INVENTION

In the liquid chromatographic separation of mixtures into two or more components on a commercial scale, it is economically desirable to operate under conditions that maintain low elution volume to feed ratios. The reason for this is mainly due to the cost involved in distilling the carrier and eluent from the feed components after they have been eluted from the chromatographic column; this cost increasing as the elution volume to feed ratio increases. One of the main causes of high elution volumes in these processes is related to the phenomena that peaks which are eluted last from the column have larger half widths than those eluted early.

Chromatography is a process whereby components contained in a fluid mixture may be separated from the mixture. This is accomplished by the selective retardation of one or more of the components of the fluid mixture as the fluid uniformly moves through a column containing a stationary substrate. The retarding results from the distribution of the components of the mixture between the substrate and the bulk fluid as the fluid moves past the stationary phase.

One of the particular chromatographic methods employed is called elution chromatography. In this technique, the feed mixture and carrier fluid plus eluent are passed sequentially through the column. In this specification, carrier fluid is taken as liquid materials which are not significantly adsorbed by the substrate in the presence of feed mixture components. Eluent is a term to describe liquid materials which are adsorbed by the substrate and compete for adsorption sites with the feed components. This sequential passage of carrier-eluent and feed leads to a differential migration of the feed's components according to their distribution between two phases. If the components of the sample have different distribution coefficients, a separation of the components is achieved as the components will elute in sequence from the end of the stationary phase. In ordinary elution development, there is a small range of retention volumes or retardation factors for optimum separation. The distribution coefficients must be sufficiently large so that the components eluted early are not pushed off the column as an unresolved series of bands, yet the distribution coefficients must be reasonably small if excessive elution times and peak broadening are to be avoided. In addition, there must be a difference in the distribution coefficients of the component in order to effect their separation.

In prior copending application Ser. No. 386,949, a technique for the automatic gradual attainment of the elution power required for each component's separation was described as well as the benefit of operating this technique at higher temperatures. It has now been discovered that by preheating the stronger eluent-carrier mixture before its passage through the bed that even smaller elution volumes are obtained. This advantage of course means lower total elution volume to feed ratios, thus providing an improved gradient elution process which produces paraxylene at substantial savings.

DESCRIPTION OF THE PRIOR ART

It is known in the separation art that certain adsorbents generally comprising crystalline aluminosilicates can be utilized to separate certain hydrocarbons from feed mixtures. In aromatic hydrocarbons separation, in particular the separation of the $C_8$ aromatic hydrocarbons, it is generally recognized that particular crystalline aluminosilicates are useful for a given $C_8$ aromatic hydrocarbon. Illustrative of the prior art is Neuzil, U.S. Pat. No. 3,558,732, which teaches an improved adsorptive separation process, the improvement comprising employing toluene as a desorbent.

Other art workers have taught the use of different kinds of X and Y type zeolites for the separation of paraxylene from a mixture of $C_8$ aromatic isomers, see for example, Neuzil U.S. Pat. No. 3,626,020. In U.S. Pat. No. 3,636,121 to Stine et al, a dual adsorption and isomerization process for the recovery and isomerization of various $C_8$ aromatic isomers is described and diethylbenzene is the eluent preferred for operation of the process.

SUMMARY OF THE INVENTION

The present invention is directed to an improved one-column liquid chromatographic separation process for $C_8$ aromatic mixtures. The process is particularly useful and is, therefore, directed to the ultimate recovery of pure paraxylene or paraxylene and ethylbenzene in purities exceeding 99% and in which 90% of the paraxylene introduced as feed is recovered.

The process utilizes crystal aminosilicate zeolite sieves which are known to selectively adsorb paraxylene and ethylbenzene in preference to the other isomers. Such sieves include potassium exchanged type Y (KY), potassium ammonium exchanged type Y (ammonium KY) and barium potassium exchanged type Y, i.e. (Ba-K)Y. These sieves are prepared by techniques described in U.S. Pat. No. 3,696,107, said disclosure herein incorporated by reference. The preferred sieve is KY sieve when either paraxylene alone or paraxylene and ethylbenzene are sought as products.

The process includes the utilization of process steps such as contacting the feed mixture with, for example, a KY sieve under conditions to effect the preferential adsorption of paraxylene and ethylbenzene; contacting the bed of KY sieve containing said selectively adsorbed paraxylene and ethylbenzene with a carrier-eluent stream thereby affecting desorption of the adsorbed components from the bed material; recovering thereafter from the bed of KY sieve a stream or streams containing metaxylene, orthoxylene, paraxylene, ethylbenzene and mixtures thereof and ultimately recovering paraxylene and ethylbenzene as product streams.

In operating the above-described process, as has been previously described in application Ser. No. 386,949, a means of reducing and thereby minimizing total elution volume to feed ratios has been found. In actuality, the operation of the aforesaid technique results in condensing the size of the overall chromatogram by decreasing tailing of the more strongly adsorbed components. The technique thus described is carried out by means of gradient elution chromatography; which may be operated in one of three ways. In the first method, the eluent concentration in the carrier-eluent is increased in a stepwise manner with time; in a second way, gradient elution is carried out by a continuous increase in the eluent concentration in the carrier eluent with time as the feed slug proceeds through the bed. Finally, in a third, but less preferred method, gradient elution is conducted by substituting for a weak eluent with a strong eluent during the elution of the feed components; such a substitution can take place in either the stepwise or continuous manner as described above.

It has now been discovered that when the abovedescribed process is carried out by preheating the stronger eluent-carrier mixtures before their passage through the bed at temperatures of at least 160°C., there is an overall 35% reduction obtained in the elution volume to feed ratio when compared to a gradient elution case run isothermally at 130°C. Although a similar reduction in elution volume to feed ratio is obtained by utilizing the high temperature isothermal process described in Ser. No. 386,949, that reduction causes a loss of ethylbenzene recovery. The process described herein does not sacrifice any ethylbenzene recovery. Preheating the stronger eluent-carrier mixture before its passage through the bed and hence during the operation of the gradient elution process results in production of temperature waves flowing through the bed and thereby condenses the total chromatogram with the final peak of each feed slug being eluted with the hotter eluent-carrier mixture in a smaller elution volume than if the stronger eluent-carrier were not preheated. The invention, therefore, is the combination of gradient elution by increasing eluent concentration, and temperature gradient elution by the preheating of the stronger eluent-carrier mixture. This combination of techniques is seen to greatly reduce the cost of paraxylene recovery because of the carrier-eluent to feed ratios obtained.

The present invention is operable with a number of different carrier-eluent compositions, preferably, however, metadiisopropylbenzene or paradiisopropylbenzene or their mixtures are used as eluting agents in the carrier-eluent stream comprising from 10 to 100% of the eluting agent, the remainder being carrier fluid. The carrier may be any inert diluent such as paraffins having carbon atoms from $C_6$ to $C_{20}$. Nonlimiting representative examples of paraffins useful as diluents are hexane, heptane, isooctane, cetane and eicosane and the like. Typically employed is n-dodecane and a typical carrier-eluent stream is a composition of about 25% metadiisopropylbenzene and 75% n-dodecane. In operating the gradient elution technique, the beginning 25% concentration of the eluting agent in the carrier-eluent may be increased to a final concentration of up to about 95%.

The present invention is operable under a wide range of conditions. For example, pressures are not critical and the present process may be operated at pressures from 0.1 to 50 atmospheres, preferably from 0.1 to 10 atmospheres, most preferably, from 1 to 5 atmospheres. In applying the present invention to commercial liquid chromatographic separations of the $C_8$ aromatic isomers particular conditions employed, such as optimum eluent, length of column, flow rate, sieve, etc., will vary from case to case.

However, in the operation of the present invention, it has been found that a feed slug size of about 2.0 cc is optimum when a 9 foot long, 0.18 inch I.D. column packed with 20–40 mesh KY (potassium-Y) sieve, m-diisopropylbenzene/dodecane as carrier-eluent is employed at a flow rate of 0.3 feet per minute and at temperatures of from 130° to about 200°C. The resultant process demonstrates that the efficiency with which paraxylene is recovered is greatly improved.

The present process is also operable with or without recycle where recycle is defined as the amount of a material recycled divided by the fresh feed times 100. Recycling can be in the range of from 10 to 100%, preferably from about 10 to 75%.

Moreover, the process while in a preferred manner, is described as an improvement for the single column liquid chromatographic process, the operation of the various embodiments described herein are also useful as an improvement over the two column scheme defined in copending application Ser. No. 282,983, now U.S. Pat. No. 3,843,518, wherein critical feed slug sizes are utilized of from at least twice, preferably at least four times, the maximum feed slug employed to obtain three pure components in a single column scheme.

In a typical processing scheme, the gradient elution-temperature elution technique for increasing the strength of the eluting agent in a liquid carrier and thereafter preheating said stronger eluting agent-carrier mixture before it is passed through the bed is carried out as follows. First of all, the technique for increasing the strength of the eluting agent in the liquid carrier may be accomplished by increasing, in a stepwise manner, from 25 to 90% the amount of eluting agent in the carrier. The process is carried out by utilizing a column containing a KY sieve through which is passed a carrier-eluent composed of, for example, 20% metadiisopropylbenzene and 80% n-dodecane at a linear velocity of 0.3 feet per minute at a column temperature of 130°C. The carrier-eluent flow is stopped after the column has been sufficiently purged and a feed slug composed of 20% paraxylene, 20% orthoxylene, 20% ethylbenzene and 40% metaxylene is injected into the column.

The chromatograph development showing the separation of components is illustrated in FIG. 1.

After feed slug injection, the carrier-eluent ($D_1$) flow is immediately resumed; said carrier-eluent ($D_1$) is normally at 130°C; the composition of the carrier-eluent stream is changed to $D_2$ in a stepwise manner by means of a three-port, two-way valve from a separate storage vessel containing 100% m-DIPB; said carrier-eluent ($D_2$) is preheated to about 160°C prior to its injection into the column. The change in composition of the carrier-eluent stream to $D_2$ is effected at a definite time period after the column composition profile of FIG. 1A is obtained. The effect of $D_2$ on the elution development of the feed slug in the column is illustrated in FIG. 1B and it is shown that p-xylene is eluted (desorbed) more quickly, while m-xylene and o-xylene are removed as product stream. A definitive volume of $D_2$ is passed through the column and is followed by subsequent feed slug injection including utilization of carrier-eluent stream $D_1$. The profile of the column composition as shown in FIG. 1C illustrates the removal of ethylbenzene as a product stream; FIG. 1D shows p-xylene removed as product stream together with desorbent $D_2$. The definite time period referred to above, where $D_1$ is changed to $D_2$, is a function of temperature, flow rate, column size, desorbent and sieve. Said time period must be chosen such that the p-xylene peak elutes from the column predominately in the presence of the higher temperature desorbent $D_2$. Although FIG. 1 is the same as FIG. 1 of Ser. No. 386,949, the volume of $D_2$ needed in the process described herein is less than that of $D_2$ needed in Ser. No. 386,946 because of the lower temperature of $D_2$ in the latter case.

When the gradient elution technique is being utilized by means of a continuous increase in the concentration of the eluting agent in the carrier-eluent stream, a typical processing scheme will be carried out similar to the scheme described above except that instead of stepwise transition from $D_1$ to $D_2$; the initial composition of carrier-eluent $D_1$ is changed continuously until composition $D_2$ is obtained, with carrier-eluent $D_2$ at a higher temperature than carrier-eluent $D_1$. This may be carried out by conventional means such as the use of a mixing tee and varying flow rates of two streams $D_1$ and $D_2$ to produce any desired change from $D_1$ to $D_2$.

The third gradient elution method or substitution technique is conducted similar to the schemes described above except that $D_2$ is 25–100% of a strong eluent such as orthodichlorobenzene (ODCB) while $D_1$ is 25–100% of a weak eluent such as meta-diisopropylbenzene (m-DIPB) or para-diisopropylbenzene (p-DIPB), with carrier-eluent $D_2$ again at a higher temperature than carrier-eluent $D_1$.

The present invention will be more easily understood by reference to FIG. 2.

In FIG. 2, representing a typical commercial-scale application of the invention, the feed slug, stream 1, is introduced into a chromatographic column. The feed slug is followed by weak desorbent, stream 14. The strong desorbent, stream 15, is preheated to a temperature higher than the column temperature and is subsequently introduced at such a time and for such a duration that the most strongly held component of the feed (i.e. paraxylene) is eluted in a stream containing essentially only strong desorbent. Product recovery is achieved by directing the eluted streams to separate fractionation facilities. Stream 2 (first cut) is fractionated into a mixed xylene product (Stream 7), a weak desorbent bottoms (Stream 5) and a strong desorbent sidestream (Stream 6). The desorbent streams are sent to storage drums for reuse. Stream 3 (second cut) is fractionated into ethylbenzene product (Stream 9) and a weak desorbent bottoms (Stream 8). Stream 4 (third cut) is fractionated into paraxylene product (Stream 13) and a strong desorbent bottoms (Stream 12). If desired, Stream 16 containing a mixture of ortho- and metaxylene and ethylbenzene can be recycled with fresh feed in order to increase ethylbenzene recovery. For the fractionation scheme shown, both the weak and strong desorbents must have higher boiling points than the products, and the strong desorbent must have a lower boiling point than the weak desorbent. This is true for 100% metadiisopropylbenzene as the strong desorbent and a mixture of metadiisopropylbenzene and tridecane as the eluent-carrier in the weak desorbent.

To further illustrate the improved process of the present invention, the following examples are provided, however, it is to be understood that the details thereof are not to be regarded as limitations, as they may be varied as will be understood by one skilled in the art.

EXAMPLE 1

Potassium Y sieve was ground to 20–40 mesh and about 30 grams were loaded into a 9 foot long, 0.25 inch O.D., 0.18 inch I.D. stainless steel column. A carrier-eluent mixture of 25% m-diisopropylbenzene and 75% n-$C_{12}$ paraffin was fed through the column at 130°C. at a flow rate of 1.5. The carrier-eluent flow was stopped and a 2.0 cc sample of 20% paraxylene, 20% ethylbenzene, 20% orthoxylene and 40% metaxylene was injected into the system upstream of the packed column through a sixport sample loop valve. Carrier-eluent flow was restarted immediately and samples of the stream eluting from the end of the column were taken periodically. Twenty minutes after the feed was injected a carrier-eluent of 100% m-diisopropylbenzene was fed through the column at 130°C at a flow rate of 1.5.

Each sample taken was analyzed for the weight percent of the $C_8$ aromatics by gas chromatography. Results showed that pure ethylbenzene (free of other $C_8$ isomers) was recovered and that the total elution volume for the $C_8$ aromatic isomers was 90 cc.

EXAMPLE 2

The procedure of Example 1 is repeated except that the carrier-eluent consisting of 100% m-diisopropylbenzene was fed through the column after the carrier-eluent was heated to 160°C. The elution volume is decreased from 90 cc in Example 1 to 75 cc in Example 2 while the ethylbenzene recovery is identical in both cases, that is, 30% of the ethylbenzene fed to the column.

EXAMPLE 3

The procedure of Example 1 is repeated except that the column temperature and desorbent temperatures are kept constant at 160°C. The elution volume is decreased from 90 cc in Example 1 to 66 cc in Example 3, but the ethylbenzene recovery decreases to 10% of the total ethylbenzene injected.

EXAMPLE 4

The procedure of Examples 1 through 3 are repeated except that 75% metadiisopropylbenzene-25% paradiisopropylbenzene is substituted for the carrier-eluent stream. Substantially the same results as obtained in Examples 1 through 3 are reproduced.

EXAMPLE 5

The procedures of Examples 1 through 3 are repeated using ammonium KY as the adsorbent instead of KY sieve. Substantially the same results and effects are observed as in Examples 1 through 3.

What is claimed is:
1. In a liquid chromatographic separation process of up to two components contained in admixture in a feedstream including the steps of:
  a. contacting the feedstream mixture containing said components to be separated with a bed of crystalline aluminosilicate adsorbent at conditions to effect the selective retention of up to two of the components by said adsorbent;
  b. passing through said bed an eluent selected from the group consisting of aromatics and substituted aromatics;
  c. increasing the strength of the eluting agent during the operation of step (b) above to thereby effect desired separation under conditions that cause low elution volume to feed ratios;

d. recovering from said bed a stream or streams containing a portion of the less preferentially adsorbed components; and e. recovering a stream or streams substantially enhanced in concentration of said selectively adsorbed components relative to other feedstream components wherein the improvement comprises preheating the eluting agent of step (c) above prior to passing it through said bed at temperatures of from about 160° to about 200°C to thereby effect the desired separation of one of said preferentially adsorbed components under conditions resulting in substantially lower elution volume to feed ratios without a corresponding substantial decrease in the separation of the other of said preferentially adsorbed components.

2. The process of claim 1 wherein said feedstream mixture is a $C_8$ aromatic feedstream containing ethylbenzene and where said crystalline aluminosilicate adsorbent is a potassium Y aluminosilicate.

3. The process of claim 2 wherein said selectively adsorbed components are paraxylene and ethylbenzene.

4. The process of claim 3 wherein the initial concentration of said eluent is about 25% and is increased to a final concentration in the range of from about 50 to about 100% during the operation of steps (b) and (c).

5. In a liquid chromatographic process for the separation of paraxylene from a feedstream containing a $C_8$ aromatic isomer mixture in ethylbenzene including the steps of:

a. contacting said feedstream with a bed of crystalline aluminosilicate adsorbent at conditions to effect the selective retention of paraxylene by said adsorbent;

b. passing through said bed an eluent selected from the group consisting of aromatics and substituted aromatics;

c. increasing the strength of the eluent in a liquid carrier containing said eluent during operation of step (b) above;

d. recovering from said bed a stream or streams containing a portion of the less preferentially adsorbed feedstream components; and e. recovering a stream or streams substantially enhanced in concentration of paraxylene wherein the improvement comprises preheating the eluting agent of step (c) above prior to passing it through said bed at temperatures of from about 160° to about 200°C to thereby effect the desired separation of one of said preferentially adsorbed components under conditions resulting in substantially lower elution volume to feed ratios without a corresponding substantial decrease in the separation of the other of said preferentially adsorbed components.

6. In a liquid chromatographic separation process for the separation of paraxylene contained in a $C_8$ aromatic isomer mixture containing ethylbenzene including the steps of:

a. contacting a $C_8$ aromatic isomer mixture with a bed containing a type Y molecular sieve selected from the group consisting of potassium Y, ammonium/potassium Y and barium potassium Y at conditions to effect the selective retention of paraxylene by said sieve;

b. passing through said sieve an eluent selected from the group consisting of metadiisopropylbenzene, paradiisopropylbenzene and toluene;

c. increasing the strength of the eluent and the liquid carrier containing said eluent during the operation of step (b) above;

d. recovering from said bed a stream or streams containing a portion of the feedstream components less preferentially adsorbed by said sieve;

e. recovering a stream or streams substantially enhanced in concentration of paraxylene wherein the improvement comprises preheating the eluting agent of step (c) above prior to passing it through said bed at temperatures of from about 160° to about 200° to thereby effect the desired separation of one of said preferentially adsorbed components under conditions resulting in substantially lower elution volume to feed ratios without a corresponding substantial decrease in the separation of the other of said preferentially adsorbed components.

7. The process of claim 6 wherein said less preferentially adsorbed components are selected from the group consisting of metaxylene, orthoxylene and ethylbenzene.

8. The process of claim 6 wherein said eluent is metadiisopropylbenzene and is employed in admixture with an inert diluent selected from the group consisting of $C_6$ to $C_{20}$ paraffins.

9. The process of claim 8 wherein the composition of said eluent/diluent admixture is 25% metadiisopropylbenzene and 75% diluent.

10. The process of claim 9 wherein said diluent is n-dodecane.

* * * * *